(12) United States Patent
Prandi et al.

(10) Patent No.: US 8,894,650 B2
(45) Date of Patent: *Nov. 25, 2014

(54) RADIUS PLATE ASSEMBLY

(71) Applicant: Memometal Technologies, Bruz (FR)

(72) Inventors: Bernard Prandi, Rennes (FR); Gregoire Chick, Carouge (CH); Jean Michel Cognet, Reims (FR); Xavier Martinache, Reims (FR); Michaël Papaloïzos, Geneva (CH); Alain Tchurukdichian, Dijon (FR)

(73) Assignee: Memometal Technologies (FR)

(*) Notice: Subject to any disclaimer, the term of this patent is extended or adjusted under 35 U.S.C. 154(b) by 0 days.

This patent is subject to a terminal disclaimer.

(21) Appl. No.: 13/796,256

(22) Filed: Mar. 12, 2013

(65) Prior Publication Data

US 2013/0197519 A1 Aug. 1, 2013

Related U.S. Application Data

(63) Continuation of application No. 12/948,795, filed on Nov. 18, 2010, now Pat. No. 8,419,776.

(30) Foreign Application Priority Data

Mar. 8, 2010 (FR) ...................................... 10 00936

(51) Int. Cl.
*A61B 17/56* (2006.01)
*A61B 17/58* (2006.01)
*A61B 17/80* (2006.01)
*A61F 2/30* (2006.01)

(52) U.S. Cl.
CPC ............. *A61B 17/80* (2013.01); *A61B 17/8004* (2013.01)

USPC .............................................. 606/71; 606/282

(58) Field of Classification Search
USPC ...................... 606/70, 71, 280, 282, 295, 296
See application file for complete search history.

(56) References Cited

U.S. PATENT DOCUMENTS

| 2,526,959 A | 10/1950 | Lorenzo |
| 2,580,821 A | 1/1952 | Nicola |
| 3,304,937 A | 2/1967 | Callender, Jr. |

(Continued)

FOREIGN PATENT DOCUMENTS

| EP | 0362049 A1 | 4/1990 |
| EP | 0410309 A1 | 1/1991 |

(Continued)

*Primary Examiner* — Andrew Yang
(74) *Attorney, Agent, or Firm* — Lerner, David, Littenberg, Krumholz & Mentlik, LLP

(57) ABSTRACT

An assembly for reducing a fracture between an epiphysis and a diaphysis of a bone has a bone plate having a fan-shaped outer end formed with a plurality of outer holes and a bar-shaped inner end extending along a longitudinal axis from the outer end and formed with a plurality of inner holes. The plate further is formed on the bar-shaped inner end with a longitudinally extending through going guide slot and between the guide slot and the outer holes with an aperture. A slide has a longitudinally extending leg with an inner end formed with a guide formation engaged into and longitudinally slidable along the guide slot and a crosspiece overlying the aperture and engaging the bone plate to both transverse sides of the aperture. The crosspiece is formed with a transversely elongated slide slot, and a slide screw engaged through the slide.

20 Claims, 3 Drawing Sheets

(56) References Cited

U.S. PATENT DOCUMENTS

| | | |
|---|---|---|
| 3,386,437 A | 6/1968 | Treace |
| 3,488,779 A | 1/1970 | Christensen |
| 3,489,143 A | 1/1970 | Halloran |
| 3,604,414 A | 9/1971 | Borges |
| 3,842,825 A | 10/1974 | Wagner |
| 3,900,025 A | 8/1975 | Barnes, Jr. |
| 4,454,876 A | 6/1984 | Mears |
| 4,506,662 A | 3/1985 | Anapliotis |
| 4,867,144 A | 9/1989 | Karas et al. |
| 4,988,350 A | 1/1991 | Herzberg |
| 5,006,120 A | 4/1991 | Carter |
| 5,041,113 A | 8/1991 | Biedermann et al. |
| 5,197,966 A | 3/1993 | Sommerkamp |
| 5,304,180 A | 4/1994 | Slocum |
| 5,324,290 A | 6/1994 | Zdeblick et al. |
| 5,380,327 A | 1/1995 | Eggers et al. |
| 5,462,547 A | 10/1995 | Weigum |
| 5,474,553 A | 12/1995 | Baumgart |
| 5,487,743 A | 1/1996 | Laurain et al. |
| 5,531,745 A | 7/1996 | Ray |
| 5,586,985 A | 12/1996 | Putnam et al. |
| 5,665,089 A | 9/1997 | Dall et al. |
| 5,681,313 A | 10/1997 | Diez |
| 5,749,872 A | 5/1998 | Kyle et al. |
| 5,827,286 A | 10/1998 | Incavo et al. |
| 5,853,413 A | 12/1998 | Carter et al. |
| 5,928,234 A | 7/1999 | Manspeizer |
| 5,951,557 A | 9/1999 | Luter |
| 5,964,763 A | 10/1999 | Incavo et al. |
| 5,968,047 A | 10/1999 | Reed |
| 6,007,535 A | 12/1999 | Rayhack et al. |
| 6,096,040 A | 8/2000 | Esser |
| 6,129,728 A | 10/2000 | Schumacher et al. |
| 6,183,475 B1 | 2/2001 | Lester et al. |
| D443,060 S | 5/2001 | Benirschke et al. |
| 6,283,969 B1 | 9/2001 | Grusin et al. |
| 6,306,136 B1 | 10/2001 | Baccelli |
| 6,325,803 B1 | 12/2001 | Schumacher et al. |
| 6,355,036 B1 | 3/2002 | Nakajima |
| 6,358,250 B1 | 3/2002 | Orbay |
| 6,364,882 B1 | 4/2002 | Orbay |
| 6,402,756 B1 | 6/2002 | Ralph et al. |
| 6,440,135 B2 | 8/2002 | Orbay et al. |
| 6,508,819 B1 | 1/2003 | Orbay |
| 6,623,486 B1 | 9/2003 | Weaver et al. |
| 6,666,867 B2 | 12/2003 | Ralph et al. |
| 6,689,134 B2 | 2/2004 | Ralph et al. |
| 6,712,820 B2 | 3/2004 | Orbay |
| 6,740,088 B1 | 5/2004 | Kozak et al. |
| 6,755,831 B2 | 6/2004 | Putnam et al. |
| 6,767,351 B2 | 7/2004 | Orbay et al. |
| 6,866,665 B2 | 3/2005 | Orbay |
| 7,090,676 B2 | 8/2006 | Huebner et al. |
| 7,128,744 B2 | 10/2006 | Weaver et al. |
| 7,189,237 B2 | 3/2007 | Huebner |
| 7,201,753 B2 | 4/2007 | Schlapfer et al. |
| 7,250,053 B2 | 7/2007 | Orbay |
| 7,276,070 B2 | 10/2007 | Muckter |
| 7,294,130 B2 | 11/2007 | Orbay |
| 7,326,212 B2 | 2/2008 | Huebner |
| 7,537,604 B2 | 5/2009 | Huebner |
| 7,604,657 B2 | 10/2009 | Orbay et al. |
| 7,635,381 B2 | 12/2009 | Orbay |
| 7,648,508 B2 | 1/2010 | Lutz et al. |
| 7,695,502 B2 | 4/2010 | Orbay et al. |
| 7,704,251 B2 | 4/2010 | Huebner et al. |
| 7,740,649 B2 | 6/2010 | Mosca et al. |
| 7,744,638 B2 | 6/2010 | Orbay |
| 7,857,837 B2 | 12/2010 | Lieponis |
| 7,857,838 B2 | 12/2010 | Orbay |
| 7,867,260 B2 | 1/2011 | Meyer et al. |
| 7,909,858 B2 | 3/2011 | Gerlach et al. |
| 7,914,562 B2 | 3/2011 | Zielinski |
| 2001/0011172 A1 | 8/2001 | Orbay et al. |
| 2002/0032446 A1 | 3/2002 | Orbay |
| 2002/0055741 A1 | 5/2002 | Schlapfer et al. |
| 2002/0065517 A1 | 5/2002 | Paul |
| 2002/0111630 A1 | 8/2002 | Ralph et al. |
| 2002/0143338 A1 | 10/2002 | Orbay et al. |
| 2002/0147453 A1 | 10/2002 | Gambale |
| 2002/0156474 A1 | 10/2002 | Wack et al. |
| 2003/0040748 A1 | 2/2003 | Aikins et al. |
| 2003/0055429 A1 | 3/2003 | Ip et al. |
| 2003/0073999 A1 | 4/2003 | Putnam |
| 2003/0105461 A1 | 6/2003 | Putnam |
| 2003/0149434 A1 | 8/2003 | Paul |
| 2003/0153918 A1 | 8/2003 | Putnam et al. |
| 2003/0233093 A1 | 12/2003 | Moles et al. |
| 2004/0030339 A1 | 2/2004 | Wack et al. |
| 2004/0059334 A1 | 3/2004 | Weaver et al. |
| 2004/0059335 A1 | 3/2004 | Weaver et al. |
| 2004/0102775 A1 | 5/2004 | Huebner |
| 2004/0102776 A1 | 5/2004 | Huebner |
| 2004/0102777 A1 | 5/2004 | Huebner |
| 2004/0102778 A1 | 5/2004 | Huebner et al. |
| 2004/0106924 A1 | 6/2004 | Ralph et al. |
| 2004/0116930 A1 | 6/2004 | O'Driscoll et al. |
| 2004/0127903 A1 | 7/2004 | Schlapfer et al. |
| 2004/0153073 A1 | 8/2004 | Orbay |
| 2004/0167522 A1 | 8/2004 | Niederberger et al. |
| 2004/0181226 A1 | 9/2004 | Michelson |
| 2004/0193155 A1 | 9/2004 | Castaneda |
| 2004/0193163 A1 | 9/2004 | Orbay |
| 2004/0193164 A1 | 9/2004 | Orbay |
| 2004/0193165 A1 | 9/2004 | Orbay |
| 2004/0204713 A1 | 10/2004 | Abdou |
| 2004/0260292 A1 | 12/2004 | Orbay et al. |
| 2004/0260293 A1 | 12/2004 | Orbay et al. |
| 2004/0260294 A1 | 12/2004 | Orbay et al. |
| 2004/0260295 A1 | 12/2004 | Orbay et al. |
| 2005/0010226 A1 | 1/2005 | Grady et al. |
| 2005/0065521 A1 | 3/2005 | Steger et al. |
| 2005/0065522 A1 | 3/2005 | Orbay |
| 2005/0065523 A1 | 3/2005 | Orbay |
| 2005/0065524 A1 | 3/2005 | Orbay |
| 2005/0080421 A1 | 4/2005 | Weaver et al. |
| 2005/0085818 A1 | 4/2005 | Huebner |
| 2005/0159747 A1 | 7/2005 | Orbay |
| 2005/0165395 A1 | 7/2005 | Orbay et al. |
| 2005/0182405 A1 | 8/2005 | Orbay et al. |
| 2005/0182406 A1 | 8/2005 | Orbay et al. |
| 2005/0234458 A1 | 10/2005 | Huebner |
| 2005/0240186 A1 | 10/2005 | Orbay |
| 2005/0240187 A1 | 10/2005 | Huebner et al. |
| 2005/0267474 A1 | 12/2005 | Dalton |
| 2006/0089648 A1 | 4/2006 | Masini |
| 2006/0173458 A1 | 8/2006 | Forstein et al. |
| 2006/0229619 A1 | 10/2006 | Orbay et al. |
| 2006/0235404 A1 | 10/2006 | Orbay et al. |
| 2006/0259039 A1 | 11/2006 | Pitkanen et al. |
| 2006/0264949 A1 | 11/2006 | Kohut et al. |
| 2007/0055253 A1 | 3/2007 | Orbay et al. |
| 2007/0123886 A1 | 5/2007 | Meyer et al. |
| 2007/0162016 A1 | 7/2007 | Matityahu |
| 2007/0233114 A1 | 10/2007 | Bouman |
| 2007/0239163 A1 | 10/2007 | Strnad et al. |
| 2007/0265629 A1 | 11/2007 | Martin et al. |
| 2007/0270853 A1 | 11/2007 | Leung |
| 2007/0299448 A1 | 12/2007 | Chin et al. |
| 2008/0132960 A1 | 6/2008 | Weaver et al. |
| 2008/0140127 A1 | 6/2008 | Vasta et al. |
| 2008/0140130 A1 | 6/2008 | Chan et al. |
| 2008/0161861 A1 | 7/2008 | Huebner |
| 2008/0183172 A1 | 7/2008 | Fritzinger |
| 2008/0195240 A1 | 8/2008 | Martin et al. |
| 2009/0036931 A1 | 2/2009 | Pech et al. |
| 2009/0036932 A1 | 2/2009 | Rouyer et al. |
| 2009/0082813 A1 | 3/2009 | Long et al. |
| 2009/0118768 A1 | 5/2009 | Sixto, Jr. et al. |
| 2009/0118769 A1 | 5/2009 | Sixto, Jr. et al. |
| 2009/0118770 A1 | 5/2009 | Sixto, Jr. et al. |
| 2009/0143825 A1 | 6/2009 | Graham et al. |
| 2009/0228047 A1 | 9/2009 | Derouet et al. |
| 2009/0234359 A1 | 9/2009 | Onoue et al. |

(56) References Cited

U.S. PATENT DOCUMENTS

| | | |
|---|---|---|
| 2009/0275947 A1 | 11/2009 | Graham et al. |
| 2009/0275987 A1 | 11/2009 | Graham et al. |
| 2009/0281577 A1 | 11/2009 | Graham et al. |
| 2009/0281578 A1 | 11/2009 | Spencer |
| 2009/0299370 A1 | 12/2009 | Kiester |
| 2009/0306724 A1 | 12/2009 | Leither et al. |
| 2009/0326591 A1 | 12/2009 | Spencer, Jr. |
| 2010/0016858 A1 | 1/2010 | Michel |
| 2010/0030276 A1 | 2/2010 | Huebner et al. |
| 2010/0030277 A1 | 2/2010 | Haidukewych et al. |
| 2010/0057132 A1 | 3/2010 | Graham et al. |
| 2010/0057133 A1 | 3/2010 | Simon |
| 2010/0057134 A1 | 3/2010 | Lowry et al. |
| 2010/0063505 A1 | 3/2010 | Frigg et al. |
| 2010/0069906 A1 | 3/2010 | Schwer |
| 2010/0137868 A1 | 6/2010 | Orbay et al. |
| 2010/0152783 A1 | 6/2010 | Borostyankoi et al. |
| 2010/0179599 A1 | 7/2010 | Derouet et al. |
| 2010/0268283 A1 | 10/2010 | Orbay |
| 2010/0292696 A1 | 11/2010 | Chantelot et al. |
| 2010/0324602 A1 | 12/2010 | Huebner et al. |
| 2011/0004252 A1 | 1/2011 | Velikov |
| 2011/0071573 A1 | 3/2011 | Sixto et al. |

FOREIGN PATENT DOCUMENTS

| | | |
|---|---|---|
| EP | 0471418 A1 | 2/1992 |
| EP | 1 250 892 A2 | 10/2002 |
| FR | 742618 A | 3/1933 |
| FR | 2254298 A1 | 7/1975 |
| FR | 2367479 A1 | 5/1978 |
| FR | 2405705 A1 | 5/1979 |
| FR | 2405706 A1 | 5/1979 |
| FR | 2406429 A1 | 5/1979 |
| GB | 2245498 A | 1/1992 |
| JP | 9206310 A | 8/1997 |
| SU | 1130332 A1 | 12/1984 |
| SU | 1223901 A1 | 4/1986 |
| SU | 1683724 A1 | 10/1991 |
| SU | 1711859 A1 | 2/1992 |
| SU | 1734715 A1 | 5/1992 |
| WO | 8201645 A1 | 5/1982 |
| WO | 9747251 A1 | 12/1997 |
| WO | 0162136 A2 | 8/2001 |
| WO | 2004045389 A2 | 6/2004 |
| WO | 2004089233 A1 | 10/2004 |
| WO | 2008113191 A1 | 9/2008 |

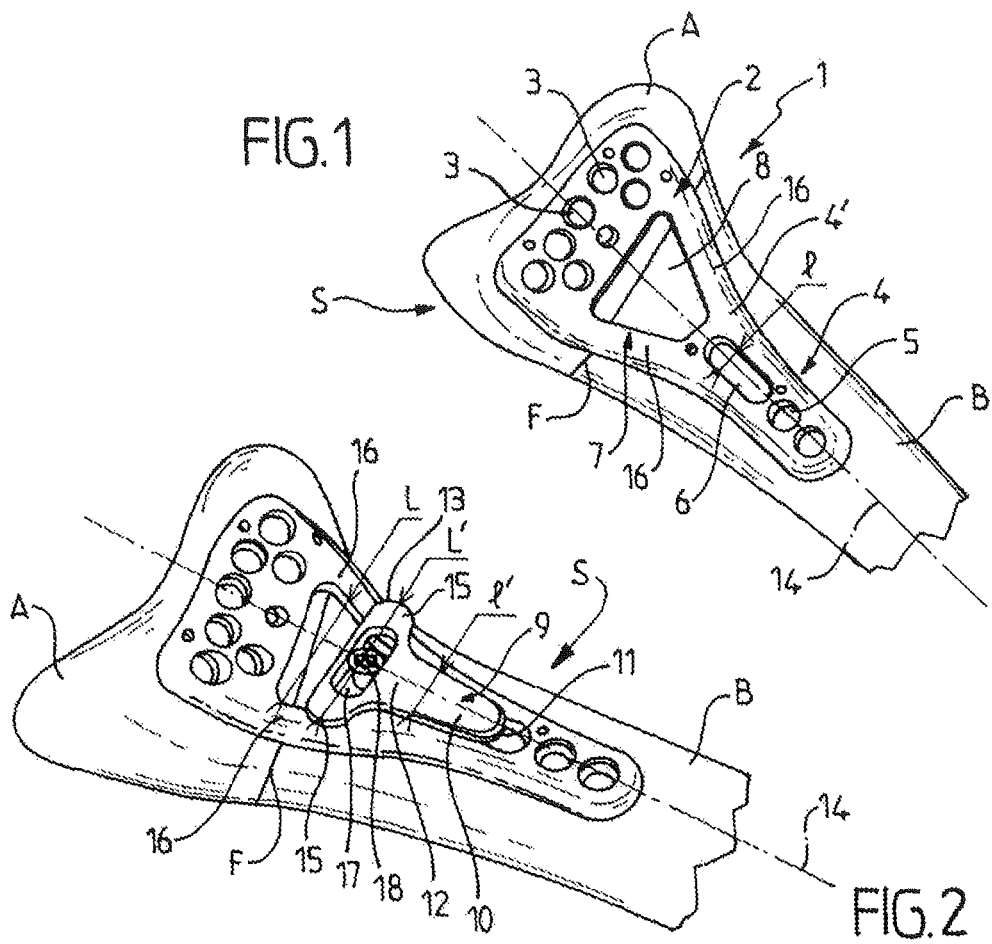
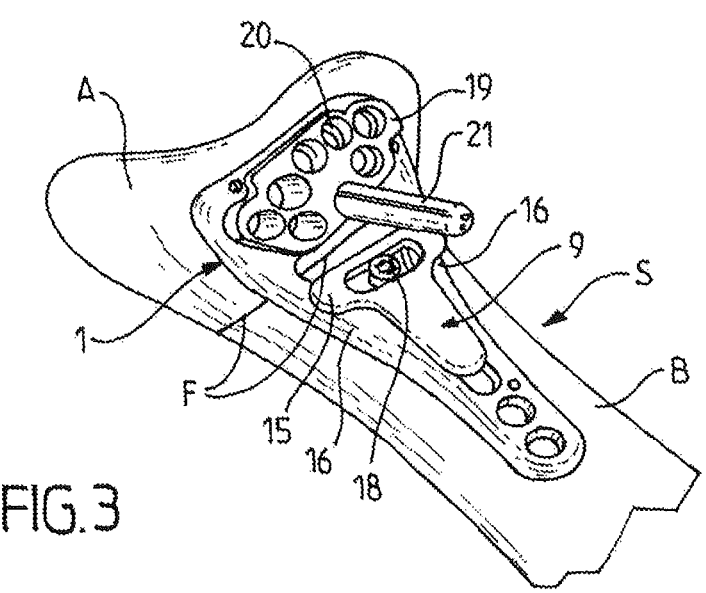

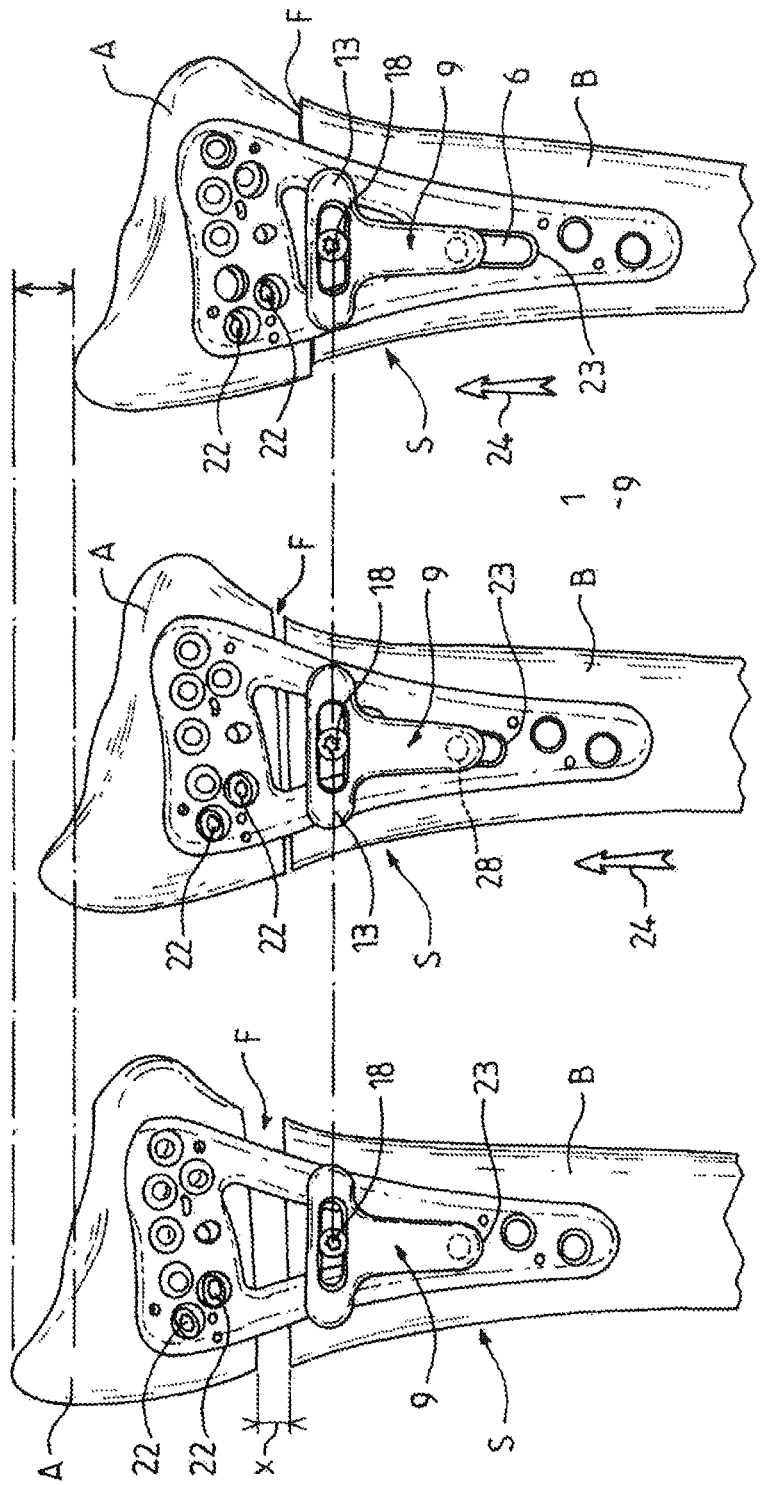

RADIUS PLATE ASSEMBLY

CROSS-REFERENCE TO RELATED APPLICATIONS

The present application is a continuation of U.S. patent application Ser. No. 12/948,795, filed Nov. 18, 2010, which is now U.S. Pat. No. 8,419,776, and which claims priority of French Patent Application No. 1000936, filed on Mar. 8, 2010, the disclosures of which are incorporated herein by reference.

FIELD OF THE INVENTION

The present invention relates to a bone plate. More particularly this invention concerns a bone-plate assembly used to secure the epiphysis or outer end of a long bone such as the radius to the bone's diaphysis or shaft.

BACKGROUND OF THE INVENTION

A typical bone plate such as described in WO 2004/089233 of Thielke, US 2006/0229619 of Orbay, US 2006/0235404, or US 2007/0055253 all of Orbay, extends along an axis and has an outer end that is fan-shaped and formed with an array of holes so that it can be solidly screwed to the epiphysis to one side of the fracture or other injury that is to be reduced so the bone can grow back together. Extending from this fan-shaped outer end is a flat narrow bar formed with another array of holes allowing it to be screwed to the bone's diaphysis. The most common use of such a bone plate is in setting or reducing a distal fracture of the radius, but it can of course also be used for any type of fracture on a distal portion of a long bone.

Because of the presence of tendons and ligaments, reducing such a break is difficult, especially considering that the more tightly the two bone parts can be engaged together the more quickly arthrodesis will mend the fracture.

The problem with such a plate is that it allows little or no adjustment once secured in place. The system of US 2007/0233114 of Bouman has transverse and longitudinal slots allowing some longitudinal and transverse shifting of parts, but in a structure intended for use on a bone shaft. It is known to form the inner bar-shaped part of the plate with an axially extending slot to allow the epiphysis and the bone plate to be shifted limitedly longitudinally of the bone to close up a fracture. Thus the orthopedic surgeon fixes the plate on the distal fragment, installs a screw loosely in the slot and pushes the distal fragment back into contact with the proximal portion of the bone, thereby making the screw slide in the hole up to the point where the two bone parts come in direct abutment with one another. In this position of the plate, the screw extending loosely through the longitudinal slot is tightened to lock in the set position.

The surgeon therefore cannot correct a transverse positioning defect, except if he redrills the proximal fragment near the first hole at an offset. In practice, this is often impossible since the two holes would be too close to one another. Therefore the transverse defect is normally left uncorrected so that the outer end of the plate overextends on the side, which can be unattractive and can cause patient discomfort.

OBJECTS OF THE INVENTION

It is therefore an object of the present invention to provide an improved bone-plate assembly usable to reduce a fractured radius.

Another object is the provision of such an improved radius plate that overcomes the above-given disadvantages, in particular that allows transverse adjustment of the epiphysis relative to the diaphysis.

A further object is to provide a surgical method of using such an assembly.

SUMMARY OF THE INVENTION

An assembly for reduction of a fracture between an epiphysis and a diaphysis of a bone has according to the invention a bone plate having a fan-shaped outer end formed with a plurality of outer holes and a bar-shaped inner end extending along a longitudinal axis from the outer end and formed with a plurality of inner holes. The plate is adapted to be screwed through the outer holes to the epiphysis and through the inner holes to the diaphysis. The plate further is formed on the bar-shaped inner end with a longitudinally extending throughgoing guide slot and between the guide slot and the outer holes with an aperture of a predetermined transverse width and of a longitudinal length generally equal to a length of the guide slot. A slide has a longitudinally extending leg with an inner end formed with a guide formation engaged into and longitudinally slidable along the guide slot and a crosspiece overlying the aperture and of a transverse width at least equal to the transverse width of the aperture such that crosspiece engages the bone plate to both transverse sides of the aperture. The crosspiece is formed with a transversely elongated slide slot, and a slide screw engaged through the slide.

Once the plate is in the correct position, the surgeon can then set the anchor screws in place in the inner and outer holes, for example with the aid of a screw/drill guide, with no risk of moving, then remove the detachable adjuster.

Therefore, although the system is complicated by the addition of a detachable element, perfect positioning is achieved.

In particular embodiments of the invention, one and/or the other following features are relevant:

the inner part is extends in a first plane and the outer part in a second plane inclined with respect to the plane of said inner part, for example by a few degrees, for example 5° to 15°, advantageously between 8° and 10°. This way, the T-slide also is form with a slight elbow and the guide pin a sufficient height to ensure guiding during the longitudinal adjustment;
the length of the guide slot is between 6 mm and 12 mm, advantageously on the order of 10 mm;
the length of the slide slot is between 12 mm and 14 mm. the width of the aperture is about 5mm at its inner end and the order of 12 mm or more at its outer end;
the substantially triangular aperture has a surface area comprised between half and ⅘th of the enlarged base of the outer part.

The system further comprises a guide for the epiphysial screws having guide holes alignable with the outer holes for the anchor screws of the outer part.

The method according to the invention has the steps of first screwing the outer part to the epiphysis through the outer holes to anchor the bone plate to the epiphysis and then screwing the slide screw through the slide slot and aperture into the diaphysis to press the adjuster against the bone plate and press the bone plate against the bone. Then the bone plate and the epiphysis it is anchored to are shifted longitudinally relative to the diaphysis with sliding of the pivot formation in the guide slot to reduce the fracture and transversely relative to the diaphysis with to correct transverse offset of the diaphysis and epiphysis at the fracture. The result can be perfect alignment without having to reset any screws.

BRIEF DESCRIPTION OF THE DRAWING

The above and other objects, features, and advantages will become more readily apparent from the following description, reference being made to the accompanying drawing in which:

FIG. 1 is a top view of a plate according to the invention on an end of a fractured radius;

FIG. 2 shows the same plate and the detachable adjuster of the system according to the invention;

FIG. 3 shows the system with a further guide for epiphysial screwing;

FIGS. 4A to 4C show the system of FIG. 2 in three different positions, showing the longitudinal adjustability according to the invention.

DETAILED DESCRIPTION

Figure 5A:
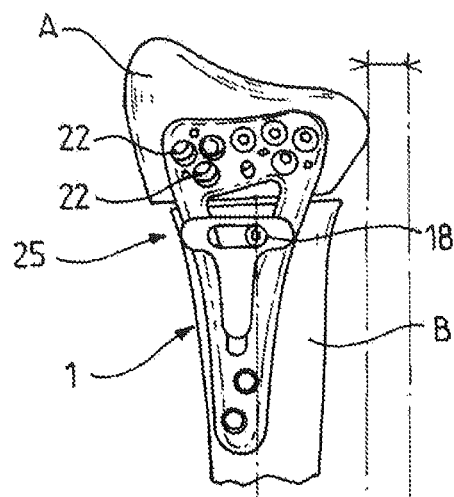
FIGS. 5A to 5C show the system of FIG. 2 in three different positions, showing the transverse adjustability according to the invention.
Figure 5B:
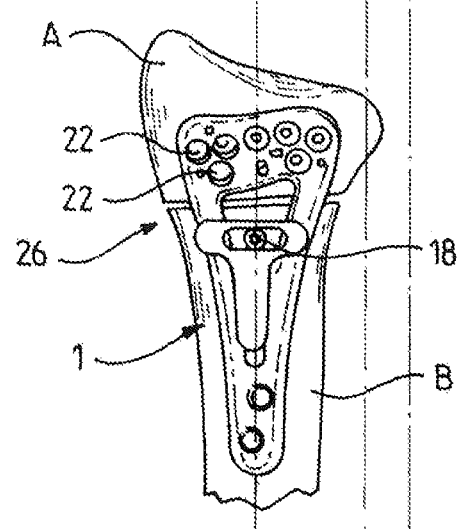

As seen in FIG. 1 a system S comprises a metal plate 1 having a fan-shaped outer part 2 for reducing a fracture F between a fractured distal end portion A of a radius and the shaft B of this bone. The plate 1 is formed with outer holes 3 for anchoring it by means of screws 22 (FIGS. 4A-5C), for example eight holes 3 in two rows of predetermined dimensions and at specific places on the end of the fan-shaped outer part 2 as is known per se. The plate 1 also is unitarily formed of an elongated bar-shaped inner part 4 extending along a longitudinal axis 14 and provided with second holes 5, for example two holes for respective unillustrated anchor screws also known per se.

The inner part 4 is further formed with an elongated, throughgoing, and longitudinally extending slot 6, for adjusting position of the plate 1 on the radius A, B parallel to the axis 14.

Here as visible in FIG. 3 the outer paddle- or fan-shaped end 2 lies generally in a plane forming an obtuse angle of between 165° and so to a plane of the narrow stem or inner part 4 of the plate 1.

According to the invention, the outer part 2 further has an inner portion 7 of generally trapezoidal shape and fixed to the outer end 4' of the inner part 4. It is formed with a substantially triangular or trapezoidal aperture 8.

As shown in FIG. 2, the system S further comprises a movable T-shaped adjuster slide 9 having a longitudinally extending leg 10 of a width 1' in an outer region 12 greater by about 2 mm than a width 1 of the parallel-sided slot 8. The leg 10 also has an inner end 11 of a width narrower than the region 12. The inner end 11 of the leg 10 is provided with a guide pin (FIG. 4B) slidable along the slot 6. This guide pin 28 is basically cylindrical and stepped with an inner end fitting slidably in the slot 6 to allow easy longitudinal sliding of the adjuster 9 on the plate 1 while still allowing as described below the adjuster 9 to pivot about an axis of the pin 28.

The T-shaped adjuster 9 further has a crosspiece 13 having a transverse width L' measured perpendicular to the longitudinal direction or axis 14 of the slot 6 or of the leg 10.

This dimension L' is greater than a maximum transverse width L of the aperture 8. The crosspiece 13 has ends 15 that are thus in contact over a sufficient distance, for example a few millimeters, with outer edges 16 of the aperture 8 of the enlarged outer part 2.

Furthermore, the crosspiece 13 is formed with a transversely elongated slot 17 with parallel, stepped, and straight inner and outer edges and circularly rounded ends.

The transverse length of this slot 17 is substantially equal to the transverse width L of the aperture 8. This slot is traversed generally centrally by a positioning screw 18 that is set in the diaphysial bone part B in a region much wider than the diameter of the screw 18. The head of this screw 18 bears downward, that is toward the bone on shoulders of the side of the slot 17 so this screw 18 secures the adjuster 9 in place against the bone plate 1 and also holds the inner part 4 of the plate 1 flatly against the diaphysis B. Thus the plate 1 can move transversely of the screw 18 set in the diaphysis B, just as longitudinal displacement of the pin 28 along the slot 6 allows for longitudinal displacement of the plate 1 as described more precisely hereinafter with reference to FIGS. 4A-4C and 5A-5C.

FIG. 3 further shows a guide 19 for setting the epiphysial screws 22 and having cylindrical guide holes 20 aligned with the holes 3. The guide 19 has a handle or rod 21 for positioning and maintaining the guide 19 in position during drilling of the pilot holes for the screws 22.

FIGS. 4A to 4C show how the longitudinal adjustment is done.

Here, the function of the T-shaped slide 9 is to adjust the longitudinal spacing between the portions A and B before or after the epiphysial screws 22 have been set to anchor the outer part 2 solidly on the outer bone part A. The degree of longitudinal adjustment is equal to the longitudinal length of the slot 6 minus the diameter of the part of the guide pin 28 engaged in the slot 6.

FIG. 4A shows a first position in which the guide pin 28 of the leg 10 of the T-shaped adjuster 9 abuts an outer end 23 of the slot 6. The fractured distal end or epiphysis A of the radius is meanwhile fixed by one or two of the screws 22 to the outer end 2 of the plate 1 to fix the plate 1 on the bone part A. In this end position, the fractured distal portion A of the radius is at a spacing x from the proximal portion B of the bone.

As the plate 1 is shifted inward relative to the adjuster 9 that is longitudinally fixed by the screw 18, this screw 18 shifts along the slot 6 (see FIG. 4B) outward in the direction of arrow 24 along with the slide 9 to bring the fractured portion A closer to the shaft part B until the spacing x as shown in FIG. 4C is completely eliminated and the fracture F is reduced, that is with the part A in direct contact at the fracture F with the proximal portion B of the bone.

Figure 5C:
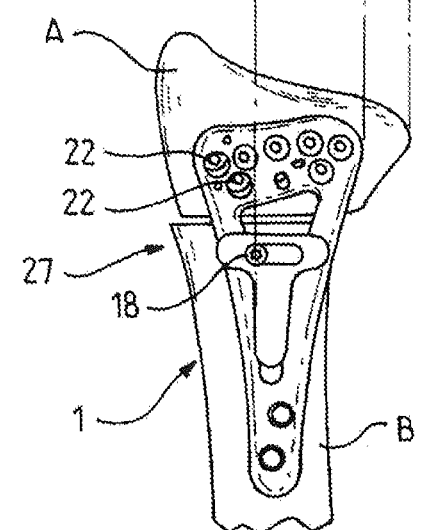

If, however, it then appears that the transverse position is incorrect, that is the parts A and B are offset transversely relative to at the fracture region F, this can be solved according to the invention as shown now in reference to FIGS. 5A and 5C that successively show a position 25 offset transversely to one side, a centered position 26, and an oppositely transversely offset position 27.

Because the plate 1 can shift transversely relative to the pin 28 engaged in the slot 27, the outer part 2 of the plate 1 secured by the screws 22 to the fractured portion A can move transversely relative to the elongated inner bone part B in such a way that it is in the desired centered position 26.

The overall procedure for setting in place an osteosynthesis system according to the invention will now be described hereinafter with reference to FIG. 3.

After two or three of the epiphysial screws 22 have been inserted in the holes 20, a first control of the assembly 5 on the end of the radius is carried out by x-ray.

According to the invention if, after the epiphysial screws 22 have been fixed, the epiphysis/diaphysis position is not right, the position can be corrected without disassembling the epiphysial zone.

To do so, with the screw 18 of the element 13 or slider loosened a bit, the plate 1 shifted transversely relative to the pin 18 for transverse correction and slid along this pin 18 for longitudinal (axis 14) correction to the right position of the portions A and B relative to each other. Then the screw 18 can be tightened to temporarily fix this position.

The other epiphysial screws are then inserted after the correct position of the plate 1 has been found and two proximal diaphysial screws are set in the holes 5.

Finally, the screw 18 is taken out, the slide 9 is removed, and another diaphysial screw is set in the slot 6 to solidly fix the plate 1 on both parts A and B.

The slide 9 serves to adjust the position of the plate 1 before or after the first epiphysial screws 22 are set.

The degree of adjustment is related to the longitudinal dimension of the slot 6 for longitudinal mobility, and to the transverse dimension of the slot 17 of the crosspiece 13 for transverse mobility.

The slide 9 is removed at the end of the surgery before the surgical field is closed.

It goes without saying and it also results from what precedes that the present invention is not limited to the embodiments particularly described. On the contrary, it encompasses all the alternatives and particularly those where the slide 9 is, for example, triangular.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An assembly for reducing a bone fracture comprising:
   a plate having a longitudinally extending throughgoing guide slot and an aperture; and
   a slide having a guide received within and longitudinally slidable along the guide slot and an elongated slide slot extending in a direction transverse to the guide slot for receiving a fastener to be placed through the aperture of the plate.

2. The assembly of claim 1, wherein the guide slot and the aperture have a generally equal length in the longitudinal direction.

3. The assembly of claim 1, further comprising:
   a fastener received through the slide slot of the slide and through the aperture of the plate.

4. The assembly of claim 1, wherein the plate has a fan-shaped outer end and a bar-shaped inner end extending along a longitudinal axis from the outer end.

5. The assembly of claim 4, wherein the outer end of the plate lies generally in a plane forming an acute angle with a plane in which the inner end of the plate generally lies.

6. The assembly of claim 5, wherein the acute angle is between 5 degrees and 15 degrees.

7. The assembly of claim 4, wherein the fan-shaped outer end defines a plurality of outer holes positioned distal to the aperture, the plurality of outer holes including at least a first hole distal to a second hole.

8. The assembly of claim 4, wherein the guide slot is defined by and extends through the inner end in a longitudinal direction.

9. The assembly of claim 4, wherein the aperture has an area between one-half and four-fifths of the outer end.

10. The assembly of claim 1, wherein the slide has a longitudinally extending leg and a cross-piece such that the slide is T-shaped.

11. The assembly of claim 10, wherein the cross-piece contacts the outer end on transversely opposing sides of the aperture.

12. The assembly of claim 1, wherein the aperture is generally triangular or trapezoidal.

13. A method of reducing a bone fracture comprising:
   fastening a plate to a first bone part;
   placing a slide against the plate such that a pin of the slide is received within a plate slot defined by the plate;
   positioning a fastener within a slide slot defined by the slide and within an aperture defined by the plate; and
   setting the fastener into a second bone part to press the slide against the plate and to press the plate against the second bone part.

14. The method of claim 13, wherein the plate includes a set of plate holes therethrough, further comprising:
   aligning guide holes of a guide with at least some of the plate holes;
   receiving a rod through at least one of the guide holes to maintain the position of the guide; and
   forming a pilot hole for the fastener while maintaining the guide in position.

15. The method of claim 13, further comprising:
   shifting the plate and the first bone part longitudinally relative to the second bone part such that the pin of the slide slides within the plate slot.

16. The method of claim 13, further comprising:
   shifting the plate and the first bone part transversely relative to the second bone part such that the fastener slides within the slide slot.

17. The method of claim 13, wherein a length of the slide slot is positioned transversely to a length of the plate slot.

18. The method of claim 13, wherein the plate is fastened to the first bone part through outer holes defined by the plate distal to the aperture.

19. The method of claim 13, wherein the plate has a fan-shaped outer end and a bar-shaped inner end extending along a longitudinal axis from the outer end, and wherein the outer end of the plate lies generally in a plane forming an acute angle with a plane in which the inner end of the plate generally lies.

20. The method of claim 13, further comprising:
   receiving a fastener through inner holes of the plate to fasten the plate to the second bone part, the inner holes of the plate being proximal to the aperture thereof.

* * * * *